US007269872B2

(12) United States Patent
Fattori et al.

(10) Patent No.: US 7,269,872 B2
(45) Date of Patent: Sep. 18, 2007

(54) POWERED TOOTHBRUSH HEAD

(75) Inventors: Joseph Edward Fattori, Mendham, NJ (US); John J. Gatzemeyer, Hillsborough, NJ (US); Gerardus W. H. Janssen, NY, NY (US)

(73) Assignee: Colgate-Palmolive Company, New York, NY (US)

( * ) Notice: Subject to any disclaimer, the term of this patent is extended or adjusted under 35 U.S.C. 154(b) by 605 days.

(21) Appl. No.: 10/121,261

(22) Filed: Apr. 12, 2002

(65) Prior Publication Data

US 2003/0192139 A1 Oct. 16, 2003

(51) Int. Cl.
*A46B 9/04* (2006.01)
*A61C 17/22* (2006.01)

(52) U.S. Cl. .......................... 15/22.1; 15/28; 15/167.1; D4/101

(58) Field of Classification Search ............... 15/167.2, 15/167.1, 207.2, 22.2, 28, 22.1; D4/101, D4/105, 109, 111, 128, 127, 132; 206/362.2
See application file for complete search history.

(56) References Cited

U.S. PATENT DOCUMENTS 1,896,731 A * 2/1933 Lippett .......................... 15/28
2,242,743 A * 5/1941 Brown
3,085,273 A * 4/1963 Cowan
4,081,876 A 4/1978 Pugh
5,046,213 A * 9/1991 Curtis et al. ............... 15/167.1
5,341,537 A * 8/1994 Curtis et al. ............... 15/167.1
5,392,483 A * 2/1995 Heinzelman et al. ...... 15/167.1
5,813,079 A 9/1998 Halm
6,000,083 A 12/1999 Nottingham et al.
D444,629 S * 7/2001 Etter et al. ................... D4/130
6,272,714 B2 * 8/2001 Beals ........................ 15/167.1
6,360,395 B2 * 3/2002 Blaustein et al. .............. 15/28
D464,799 S * 10/2002 Crossman et al. ........... D4/104
6,564,416 B1 * 5/2003 Claire et al. ............... 15/167.1
6,725,490 B2 * 4/2004 Blaustein et al. ............ 15/22.1
2003/0140435 A1 * 7/2003 Eliav et al.
2003/0182743 A1 * 10/2003 Getzemeyer et al.
2003/0182744 A1 * 10/2003 Fattori et al.
2003/0182746 A1 * 10/2003 Fattori et al.

FOREIGN PATENT DOCUMENTS

WO WO99 23910 5/1999

* cited by examiner

*Primary Examiner*—Mark Spisich
(74) *Attorney, Agent, or Firm*—Michael Wallace, Jr.

(57) ABSTRACT

A toothbrush head containing a first oscillating or rotating bristle bearing section in combination with a static bristle bearing section fixedly mounted to said head, wherein there are at least two bristles located on said static section which are oriented at different angles to the face thereof.

17 Claims, 3 Drawing Sheets

18 14 24 12 30 20 16 26

13
10
12
24
20
14
22
16

12
24
26
14
16
18
20
30

12
28
24
26
42
14
16
20
18
40
32
30

POWERED TOOTHBRUSH HEAD

BACKGROUND OF THE INVENTION

The present invention is directed to a powered toothbrush head that includes an oscillating block having bristles extending therefrom. Various types of such powered toothbrushes are generally known in the art which provide for cleaning and massaging of both the soft and hard tissue of the mouth. Reference is made to U.S. Pat. No. 5,625,916 which relates to an electrically driven toothbrush which includes a motor drive for rotating a drive shaft. The drive shaft is connected to a bristle holder on the head of the toothbrush in such a manner that rotation of the drive shaft causes the bristle holder to rotationally oscillate back and forth. Various other arrangements are known for oscillating a bristle holder mounted to the head of an electric toothbrush.

Published PCT application WO 02/19942 discloses a motor-driven toothbrush with a conventionally oscillating, round facial cross-section brush head from which extend a plurality of bristles. The brush head is divided into a number of brush support segments, which segments are arranged so as to be displaced relative to each other, such that the angle of the bristles within each segment of the brush head will vary during use.

U.S. Pat. No. 5,046,213 discloses a manual toothbrush with a brush face having extending therefrom a combination of bristle tufts some of which are substantially perpendicular to the brush face, some of which tilt laterally inward toward the center of the face and some of which tilt laterally outward toward the nearest side of the brush face. This combination of multiply angled bristles is disclosed to provide a dynamic cleaning effect, as the bristles are forced in the direction of their angle, they will tend to spring out of crevasses within and between the teeth as stresses are exceeded to contain them in place. This dynamic cleaning effect will tend to fling plaque out of such crevasses.

There is a need in the art for an electric toothbrush which contains a combination of moving and non-moving bristles, wherein at least some of the non-moving bristles are at different angles to provide the cleaning and massaging effects of an electric toothbrush and the dynamic cleaning effect of multiply angled non-moving bristles.

SUMMARY OF THE INVENTION

An object of the present invention is to provide a powered toothbrush head with a face containing a combination of a conventional oscillating or rotating bristle block or section capable of delivering the cleaning and massaging benefit expected of a conventional powered toothbrush, in combination with a second bristle block or section containing plurality of non-moving bristles which are oriented at, at least, two or more angles to the face to provide a dynamic cleaning action.

In accordance with this invention the toothbrush head has mounted on its face a conventional oscillating bristle block or section which has an outer surface, i.e. facial cross-section, that is generally circular or egg-shaped. This first bristle section is mounted in such a manner as to spin or oscillate back and forth preferably rotationally. The head includes a second bristle section, wherein the bristles are static or non-moving, i.e. mounted on a section of the brush face which is permanently fixed to the brush head. The second bristle section contains at least two sets of bristles oriented at different angles to the brush face.

THE DRAWINGS

DETAILED DESCRIPTION

Figure 1:
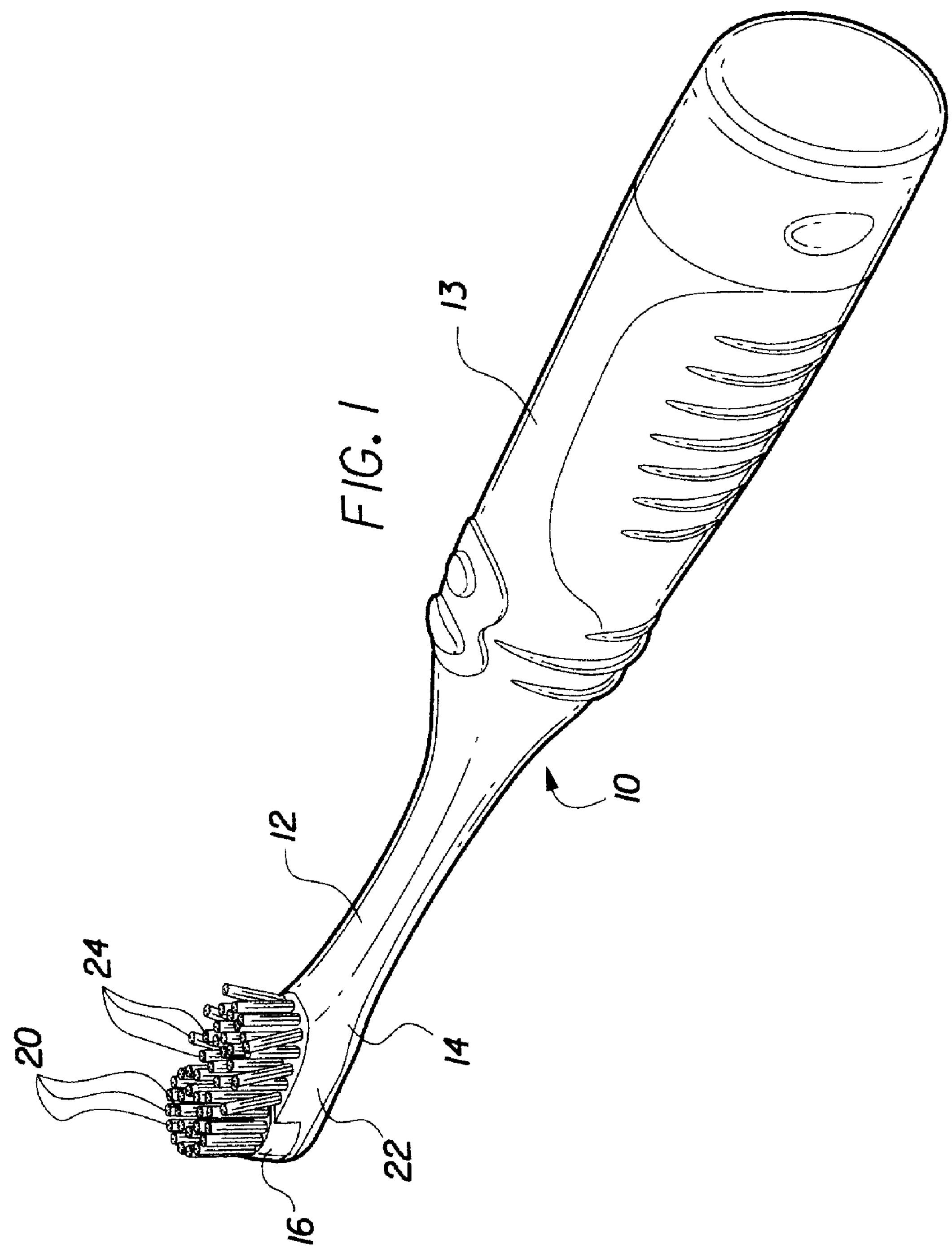
FIG. 1 is a perspective view of a powered toothbrush head in accordance with this invention.

FIG. 1 illustrates one practice of this invention wherein a toothbrush 10 includes a neck section 12 of a handle 13 and a head 14. The head 14/neck 12 may be replaceable, i.e. a refill head or the head 14/neck 12 section may be permanently attached to the handle 13 within the practice of this invention.

Figure 2:
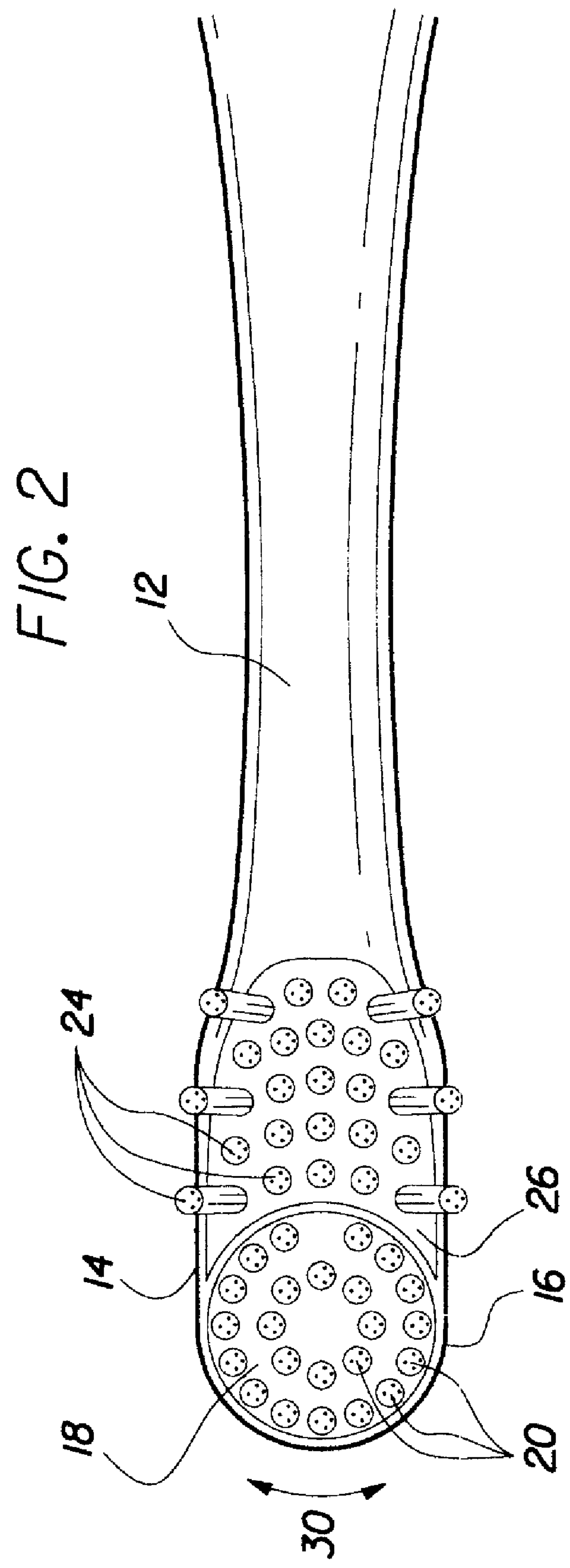
FIG. 2 is a front elevational view of the head shown in FIG. 1.

As also illustrated in FIG. 2 a first moving bristle section or block 16 is mounted on head 14 with a plurality of bristles grouped into bristle tufts 20 extending generally perpendicular from the face 18 thereof. Bristle block 16 is preferably a generally circular type disk which may be mounted on a pin for rotation about a centrally located axis parallel to axis (not shown). Bristle block 16 is mounted for rotation or for oscillation in a back and forth manner as indicated by arrow 30. Any suitable drive structure could be used for oscillating tuft block 16, such as disclosed in U.S. Pat. No. 6,000,083 or that disclosed in PCT publication WO 01/19281. A preferred type of drive structure is disclosed in U.S. Pat. No. 5,625,916, all of the details of which are incorporated herein by reference thereto. U.S. Pat. No. 5,625,916 includes a drive shaft which is driven from a motor in handle 13. The drive shaft terminates in a bent drive end located in a slot in tuft block 16. As the drive shaft is rotated, the uni-directional rotation of the drive shaft and the rotation of the drive end are transmitted to the bristle block 16 as a reciprocating rotational motion indicated by the arrow 30.

Figure 3:
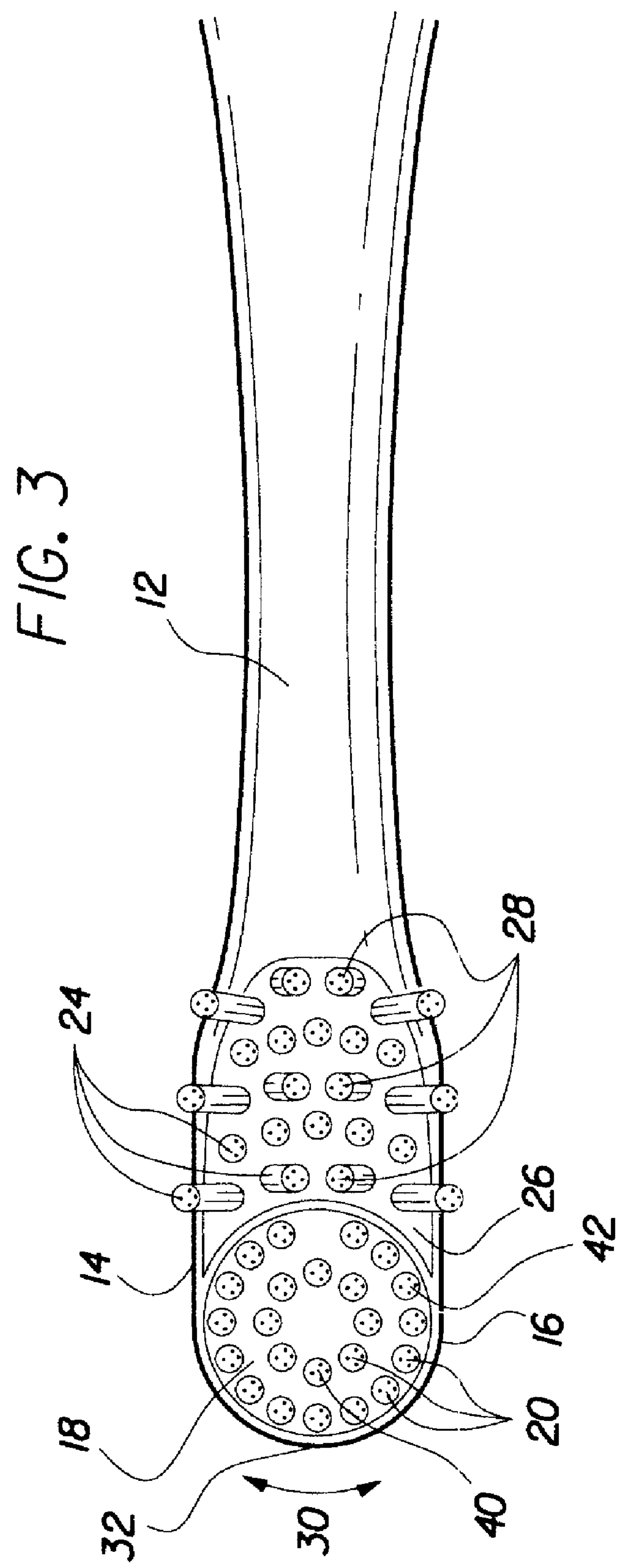
FIG. 3 is a front elevational view of a second embodiment of the powered toothbrush head of the present invention.

As best seen in FIG. 2, head 14 includes a second section or bristle block 22 from which extend a plurality of fixed, static or stationary bristles group into tufts 24, at least two of which fixed, static or stationary bristles are oriented at different angles to the face 26 of the second bristle block 22. As shown in FIG. 2, one grouping of tufts are acutely angled to the face 26, located on the periphery of the brush head and splay out from the center of the brush head toward the sides thereof, and a second grouping of tufts are oriented perpendicular to the face 26. An alternative embodiment is shown in FIG. 3, wherein in addition to the splayed out peripheral bristles and perpendicular bristles, there is a set of bristles 28 which are acutely angled with respect to the face 26 in a direction toward the longitudinal centerline of the brush. In the practice of the present invention there may be a fourth and fifth grouping of differently angled bristles, each grouping differently angled with respect to the brush face 26, but oriented in a different direction with respect to the brush head 14, e.g. toward the toe 32 of the brush head 14, toward the neck 12, or in any direction therebetween.

While FIGS. 1-3 illustrate the various bristle tufts to be of conventional fiber form, the terms "bristles", "tufts", or "bristle tufts" is intended to be used in a generic sense as cleaning elements or massage elements and could include, for example, elastomeric fingers or walls arranged in a circular cross-section shape or any type of desired shape or cross-section, including straight portions or sinusoidal portions.

It is to be understood that the specific illustrations of the bristles is merely for exemplary purposes. The invention can, however, be practiced with various combinations of the same or different bristle configurations embedded in the brush head 14 by known technology, such as stapled technology or in-mold tufting technology using the same or different bristle materials (such as nylon bristles, spiral bristles, rubber bristles, etc.). Similarly, while FIGS. 1-3 illustrate the bristles on the generally circular moving bristle section 16 to be generally perpendicular to the outer surface 22 of head 14, some or all of the bristles moving bristle section tufts may be angled at various angles with respect to the outer surface of the moving bristle section 16. It is thereby possible to select the combination of bristle configurations, bristle materials and bristle orientations to achieve specific intended results, such as to deliver additional oral health benefits like enhanced cleaning, tooth polishing, tooth whitening and/or massaging of the gums.

Although all of the bristles may be of the same length so that a planar brushing surface results from the various sections of head 14, the bristles could be of differing lengths. For example, the inner row of bristles 40 could be shorter than the outer row of bristles 42 on tuft block 16 so that a cup-like effect is produced which would help retain the toothpaste on the first tuft block 16.

In the practice of the present invention, the first moving tuft section 16 may be located closest to the handle 12 and the fixed, non-moving tuft section 22 may be located closest to the toe 32 of the toothbrush. Alternatively the moving section may be located between two fixed, non-moving sections (one fixed section closest to the handle 12 and the other fixed section closest to the toe of the toothbrush 32)

As illustrated in FIGS. 1-3 the face 18,26 of each of the sections of head 14 are coplanar so as to lie in a single plane. The invention may be practiced, however, where one or more sections may be in a parallel plane or even an inclined plane with respect to each other and/or with respect to the handle of the toothbrush 13.

What is claimed is:

1. A powered toothbrush comprising:

a handle with a neck and a head extending from said neck, a longitudinal centerline of the head generally extending from the neck toward a toe of the head;

a moving bristle bearing section mounted to said head; and a static bristle bearing section mounted to said head and having a face, a first, second and third row of bristles disposed substantially transverse to the longitudinal centerline of the head and curving toward the toe, said first and third rows having bristles extending from said face and being splayed away from said centerline, said second row being interposed between said first and third rows, said second row bristles extending substantially perpendicularly from the face;

wherein said moving section is connected to a drive structure which oscillates or rotates said moving section and said static section face has extending therefrom at least two bristles oriented at different angles to the face thereof.

2. The toothbrush of claim 1, wherein said static section includes two bristles, one of which is oriented perpendicular to said face and the other is oriented at an acute angle to said face.

3. The toothbrush of claim 1, wherein said static section includes at least three bristles, each of which is oriented at a different angle to said face.

4. The toothbrush of claim 1, wherein said moving section is the most distal bristle bearing section from said handle.

5. The toothbrush of claim 1, wherein said static section is the most distal bristle bearing section from said handle.

6. The toothbrush of claim 1, wherein said moving section has an outer surface which is generally circular or egg-shaped.

7. A powered toothbrush comprising:

a handle with a neck and a head extending from said neck, said head having a a longitudinal side, and a centerline generally extending from the neck toward a toe of the head;

a moving bristle bearing section mounted to said head;

a static bristle bearing section mounted to said head and having a face, a first, second and third row of bristles disposed substantially tranverse to said centerline and curving toward the toe, said first and third rows having bristles extending from said face and being splayed away from said centerline toward said longitudinal side, said second row being interposed between said first and third rows, said second row bristles extending substantially perpendicularly from the face.

8. The powered toothbrush of claim 7, wherein said first and third rows include bristles extending from said face and being splayed away from said longitudinal side toward said centerline.

9. The powered toothbrush of claim 8, wherein said bristles of said first, second and third rows extend from said face without intermingling with each other.

10. The powered toothbrush of claim 7, wherein said bristles of said first, second and third rows each have a distal end substantially disposed in the same plane.

11. The powered toothbrush of claim 7, wherein said bristles of said first and third rows include bristles extending substantially perpendicularly from said face.

12. A powered toothbrush comprising:

a handle with a neck and a head extending from said neck, said head having a longitudinal centerline generally extending from the neck toward a toe of the head;

a moving bristle bearing section mounted to said head; and a static bristle bearing section mounted to said head and having a face, said static bristle bearing section comprising:

a first row of bristles having bristles extending from said face and being splayed away from a center portion of the first row;

a third row of bristles having bristles extending from said face and being splayed away from a center portion of the third row;

a fifth row of bristles having bristles extending from said face and being splayed away from a center portion of the fifth row;

a second row of bristles extending substantially perpendicularly from said face, said second row being interposed between said first and third rows; and a fourth row of bristles extending substantially perpendicularly from said face, said fourth row being interposed between said third and fifth rows, wherein each of the rows of bristles is disposed substantially transverse to the longitudinal centerline of the head and curves toward the toe.

13. The powered toothbrush of claim 12, wherein said first row includes bristles splayed toward said center portion of said first row, said third row includes bristles splayed toward said center portion of said third row, and said fifth row includes bristles splayed toward said center portion of said fifth row.

14. The powered toothbrush of claim 13, wherein said bristles of said first, second, third, fourth and fifth rows extend from said face without intermingling with each other.

15. The powered toothbrush of claim 12, wherein said bristles of said first, second, third, fourth and fifth rows each have a distal end substantially disposed in the same plane.

16. The powered toothbrush of claim 12, wherein said bristles of said first, third and fifth rows include bristles extending substantially perpendicularly from said face.

17. The powered toothbrush of claim 12, wherein all bristles of said first, third, and fifth rows extend from said face at an acute angle to said face.

* * * * *